(12) United States Patent
Eerdmans

(10) Patent No.: US 7,374,547 B2
(45) Date of Patent: May 20, 2008

(54) DELIVERY DEVICE FOR AN ACIDITY MONITORING SYSTEM

(75) Inventor: Pedro H. A. Eerdmans, St. George (CH)

(73) Assignee: Medtronic, Inc., Minneapolis, MN (US)

( * ) Notice: Subject to any disclaimer, the term of this patent is extended or adjusted under 35 U.S.C. 154(b) by 629 days.

(21) Appl. No.: 10/424,550

(22) Filed: Apr. 25, 2003

(65) Prior Publication Data

US 2004/0215128 A1 Oct. 28, 2004

(51) Int. Cl.
*A61B 5/103* (2006.01)
*A61B 5/117* (2006.01)

(52) U.S. Cl. ........................... 600/593; 600/300

(58) Field of Classification Search ............. 600/350, 600/361, 587, 593, 309, 561, 407, 301–302, 600/476, 101, 104, 106, 109, 114–117, 143, 600/151, 160

See application file for complete search history.

(56) References Cited

U.S. PATENT DOCUMENTS

| | | | | |
|---|---|---|---|---|
| 4,030,481 A * | 6/1977 | Hill | ............................. | 600/561 |
| 4,062,360 A * | 12/1977 | Bentley | ......................... | 604/541 |
| 4,981,470 A * | 1/1991 | Bombeck, IV | .............. | 600/350 |
| 5,105,812 A | 4/1992 | Corman | | |
| 5,117,827 A * | 6/1992 | Stuebe et al. | ................ | 600/350 |
| 5,297,437 A * | 3/1994 | Schneider | ..................... | 73/705 |
| 5,339,799 A * | 8/1994 | Kami et al. | ................... | 600/117 |
| 5,411,022 A * | 5/1995 | McCue et al. | ............... | 600/361 |
| 5,964,714 A * | 10/1999 | Lafontaine | .................... | 600/561 |
| 6,113,553 A * | 9/2000 | Chubbuck | .................... | 600/561 |
| 6,358,197 B1 * | 3/2002 | Silverman et al. | ............. | 600/29 |
| 6,632,175 B1 * | 10/2003 | Marshall | ...................... | 600/309 |
| 6,689,056 B1 * | 2/2004 | Kilcoyne et al. | ........... | 600/300 |
| 6,951,536 B2 * | 10/2005 | Yokoi et al. | ................ | 600/128 |

OTHER PUBLICATIONS

Bravo pH Capsule With Delivery System, User Guide, Medtronic, 2002.
Bravo pH Receiver, User Guide, Medtronic 2002.

* cited by examiner

*Primary Examiner*—Max F. Hindenburg
*Assistant Examiner*—Rene Towa
(74) *Attorney, Agent, or Firm*—Shumaker & Sieffert, PA

(57) ABSTRACT

The invention is directed to techniques for delivering a capsule for sensing acidity to a location along the esophagus via a delivery device that detects pressure variations to identify a lower esophageal sphincter (LES). More specifically, the distal end of a probe of the delivery device enters the esophagus, and extends through the esophagus into the stomach via the LES. The distal end of the probe is slowly retracted back into the esophagus and the pressure variation within a pressure sensitive chamber of the delivery device, caused by the LES, is detected to identify the location of the LES. As described, the pressure sensitive chamber can comprise a balloon filled with air or an airtight chamber formed within a distal end of the probe. In either case, the pressure sensitive chamber deforms due to the pressure of the LES thereby causing a pressure variation used to identify the location of the LES.

20 Claims, 6 Drawing Sheets

DELIVERY DEVICE FOR AN ACIDITY MONITORING SYSTEM

FIELD OF THE INVENTION

The invention relates to medical devices and, more particularly, to medical devices for pH monitoring within the gastro-intestinal tract.

BACKGROUND OF THE INVENTION

Gastroesophageal reflux occurs when stomach acid intermittently surges into the esophagus. It is common for most people to experience this acid reflux occasionally as heartburn. Gastroesophageal reflux disease (GERD) is a clinical condition in which the reflux of stomach acid into the esophagus is frequent enough and severe enough to impact a patient's normal functioning or to cause damage to the esophagus.

In the lower part of the esophagus, where the esophagus meets the stomach, there is a muscular valve called the lower esophageal sphincter (LES). Normally, the LES relaxes to allow food to enter into the stomach from the esophagus. The LES then contracts to prevent stomach acids from entering the esophagus. In GERD, the LES relaxes too frequently or at inappropriate times allowing stomach acids to reflux into the esophagus.

The most common symptom of GERD is heartburn. Acid reflux also leads to esophageal inflammation, which causes symptoms such as painful swallowing and difficulty swallowing. Pulmonary symptoms such as coughing, wheezing, asthma, or inflammation of the vocal cords or throat may occur in some patients. More serious complications from GERD include esophageal ulcers and narrowing of the esophagus. The most serious complication from chronic GERD is a condition called Barrett's esophagus in which the epithelium of the esophagus is replaced with abnormal tissue. Barrett's esophagus is a risk factor for the development of cancer of the esophagus.

Accurate diagnosis of GERD is difficult but important. Accurate diagnosis allows identification of individuals at high risk for developing the complications associated with GERD. It is also important to be able to differentiate between gastroesophageal reflux, other gastrointestinal conditions, and various cardiac conditions. For example, the similarity between the symptoms of a heart attack and heartburn often lead to confusion about the cause of the symptoms.

Esophageal manometry, esophageal endoscopy, and esophageal pH monitoring are standard methods of measuring esophageal exposure to stomach acids and are currently used to diagnose GERD.

BRIEF SUMMARY OF THE INVENTION

The invention is directed to techniques for measuring acidity within an esophagus of a patient and, more particularly, to anchoring a capsule for sensing acidity of the esophagus to the esophageal wall. The techniques provide a method for determining an appropriate location for the capsule by obtaining pressure measurements with the same device that anchors the capsule to the esophagus. This reduces the need of an additional procedure, such as a manometry or endoscopy, before delivering the capsule.

The acidity monitoring system includes a capsule for sensing acidity and a receiver. The capsule includes an acidity sensor, e.g., a pH sensor, to measure the acidity level within the esophagus. The receiver and the capsule are in wireless communication. In particular, the capsule transmits measured acidity data to the receiver via a transmitter and an antenna. The information stored within the receiver may be downloaded by a physician to a computing device and analyzed to diagnose the condition of the patient.

A delivery device anchors the capsule to a wall of the esophagus and, more particularly, to esophageal tissue within the esophagus. The delivery device includes a handle and a flexible probe that extends from the handle into the esophagus of the patient. The capsule is coupled to a distal end of the probe for delivery to a particular location within the esophagus. In accordance with the invention, the delivery device detects pressure variances within a pressure sensitive chamber of the delivery device to identify an appropriate location for attachment of the capsule to the esophagus. More specifically, the delivery device includes a pressure sensor that measures pressure variations within the pressure sensitive chamber to identify the appropriate location for placement of the capsule.

The pressure variation occurs during placement of the probe into the esophagus of the patient. In particular, the distal end of the probe enters the esophagus, via either the nasal cavity or the oral cavity of the patient, and extends through the esophagus into the stomach via the lower esophageal sphincter (LES). The distal end of the probe is slowly retracted back into the esophagus and the pressure variation due to the LES is detected to identify the location of the LES. The capsule may be anchored to a wall of the esophagus proximate the LES. For example, the capsule can be attached to the wall of the esophagus approximately 2 centimeters (cm) above the LES.

The delivery device includes a vacuum inlet on the handle to couple the delivery device to a vacuum. The vacuum applies suction within an inner lumen formed by the probe. A vacuum outlet at the distal end of the probe and, more particularly, at the interface between the probe and the capsule, applies suction from the vacuum to the wall of the esophagus in order to draw esophageal tissue of the wall into a void within the capsule. The delivery device anchors the capsule to the esophageal tissue drawn into the void of the capsule and disengages from the capsule thereby leaving the capsule attached to the wall of the esophagus. The delivery device may, for example, advance a locking pin through the esophageal tissue captured in the void to anchor the capsule to the wall of the esophagus.

While on the wall of the esophagus, the capsule and, more particularly, the acidity sensor of the capsule obtains acidity measurements for a period of time, e.g., 24 hours, and relays the acidity measurements to the receiver via wireless telemetry. The capsule eventually self-detaches from the wall of the esophagus and is passed through the digestive system of the patient.

As will be described, prior to introducing the delivery device into the patient, the pressure sensitive chamber is formed within or proximate to the distal end of the probe in accordance with the invention. The pressure sensitive chamber can be formed within the inner lumen formed by the probe by closing the vacuum inlet and the vacuum outlet. The delivery device includes a membrane that covers the vacuum outlet preventing flow of air from the vacuum outlet. The delivery device further includes a valve that is shut to prevent flow of air through the vacuum inlet. In this manner, the vacuum inlet and outlet are shut to form the pressure sensitive chamber within the distal portion of the probe and the handle of the delivery device. The distal end of the probe can be formed from a flexible material such that the pressure applied to the distal end of the probe by the LES causes the flexible portion of the probe to deform, thereby varying the pressure within the pressure sensitive chamber. Alternatively, the delivery device can include a balloon that is filled with air to form the pressure sensitive chamber. As the pressure exerted on the outside of the balloon increases upon encountering the LES, the balloon deforms, thereby varying the pressure within the pressure sensitive chamber.

In one embodiment, the invention provides a device comprising a probe that defines an inner lumen, a capsule coupled to a distal end of the probe that includes a sensor, a pressure sensitive chamber within the inner lumen of the probe, and a pressure sensor to detect pressure variation within the pressure sensitive chamber to identify a location for delivery of the capsule.

In another embodiment, the invention provides a method comprising detecting a pressure variation within a pressure sensitive chamber of a probe, providing suction to a tissue site of a patient to draw a portion of the tissue site into a void of a capsule coupled to a distal end of the probe in response to detecting the pressure variation, anchoring the capsule to the tissue site, and detaching the capsule from the probe.

DETAILED DESCRIPTION OF THE INVENTION

Figure 1:
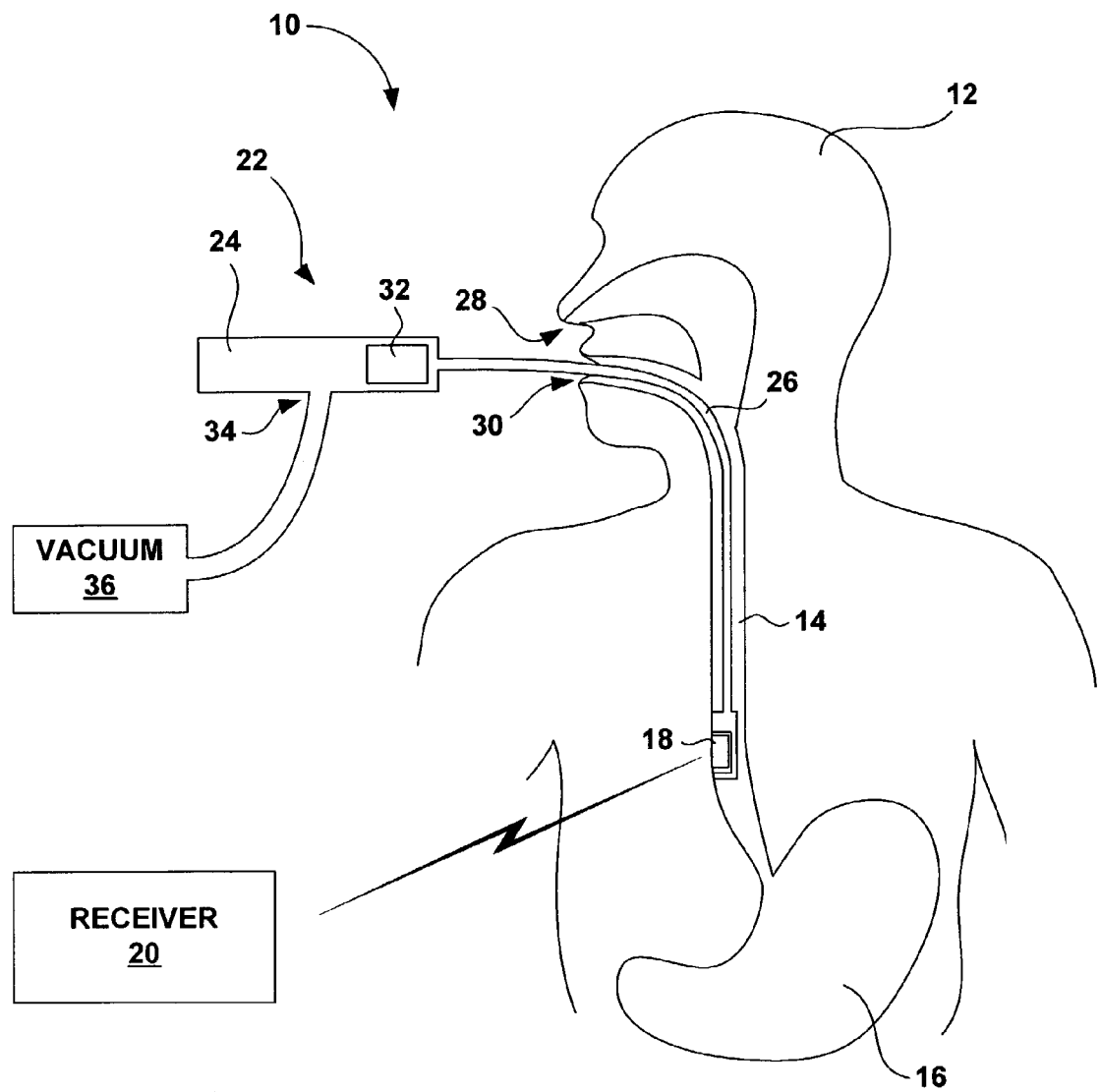
FIG. 1 is a schematic diagram illustrating an acidity monitoring system shown in conjunction with a patient.

FIG. 1 is a schematic diagram illustrating an acidity monitoring system 10 shown in conjunction with a patient 12. Acidity monitoring system 10 measures the acidity within the lower portion of an esophagus 14 of patient 12. More specifically, acidity monitoring system 10 measures the acidity level near the lower esophageal sphincter (LES) of patient 12, i.e., where esophagus 14 meets stomach 16. Measuring the acidity level of the lower portion of esophagus 14 allows a physician to more accurately diagnose Gastroesophageal Reflux Disease (GERD).

As described above, the LES normally relaxes to allow food to enter into stomach 16 from esophagus 14. The LES then contracts to prevent stomach acids from entering esophagus 14. In GERD, the LES relaxes too frequently or at inappropriate times allowing stomach acids to reflux into the esophagus 14, increasing the acidity level near the lower portion of esophagus 14, which may lead to complications such as heartburn, painful swallowing, difficulty swallowing, coughing, wheezing, asthma, inflammation of the vocal cords or throat, esophageal ulcers, narrowing of the esophagus, and in the worst cases Barrett's esophagus.

Acidity monitoring system 10 includes a capsule 18 for sensing acidity and a receiver 20. Capsule 18 includes an acidity sensor, e.g., a pH sensor, to measure the acidity level within esophagus 14. Receiver 20 and capsule 18 are in wireless communication. In particular, capsule 18 transmits measured acidity data to receiver 20 via a transmitter and an antenna (not shown). Receiver 20 may, for example, comprise a portable receiver that is carried by patient 12. The information stored within receiver 20 may be downloaded by a physician to a computing device and analyzed to diagnose the condition of patient 12.

A delivery device 22 attaches capsule 18 to a wall of esophagus 14 and, more particularly, to esophageal tissue within esophagus 14. Delivery device 22 includes a proximal portion, referred to herein as a handle 24, and a flexible probe 26 that extends from handle 24 into esophagus 14 of patient 12. Capsule 18 is coupled to a distal end of probe 26 for delivery to a particular location within esophagus 14. In accordance with the invention, delivery device 22 detects pressure variances within a pressure sensitive chamber within delivery device 22 to identify an appropriate location for attachment of capsule 18 to esophagus 14. More specifically, delivery device 22 includes a pressure sensor that measures pressure variations within the pressure sensitive chamber to identify the appropriate location for placement of capsule 18.

In particular, the distal end of probe 26 enters esophagus 14, via either nasal cavity 28 or oral cavity 30, and extends through esophagus 14 into stomach 16 via the lower esophageal sphincter (LES). The distal end of probe 26 is slowly retracted back into esophagus 14 and the pressure variation due to the LES is detected to identify the appropriate location for capsule 18. Specifically, the pressure sensitive chamber experiences pressure variations due to the LES, which indicates the location of the LES. Capsule 18 may be placed on a wall of esophagus 14 in accordance with the pressure variation measurement. For example, capsule 18 can be attached to the wall of esophagus 14 approximately 2 centimeters (cm) above the LES.

A display 32 located on handle 24 of delivery device 22 displays the pressure variations measured by the pressure sensor within delivery device 22. Display 32 may be, for example, a Liquid Crystal Display (LCD), Light-Emitting Diode (LED) display or the like. In some embodiments, display 32 displays the pressure values as a numerical value in order to allow the physician to see when the pressure variation is experienced. In other embodiments, display 32 simply displays a relative pressure variation. For example, display 32 may comprise a number of LEDs that successively light up as the pressure increases. In this manner, the physician can detect a change in pressure when the number of lit LEDs increases, e.g., from 3 lit LEDs to 5 lit LEDs.

Delivery device 22 includes a vacuum inlet 34 on handle 24 to couple delivery device 22 to a vacuum 36. Vacuum 36 applies suction within an inner lumen formed by probe 26. A vacuum outlet (not shown) at the distal end of probe 26 and, more particularly, at the interface between probe 26 and capsule 18, applies the suction from vacuum 36 to the wall of esophagus 14 in order to draw esophageal tissue into a void within capsule 18. Delivery device 22 anchors capsule 18 to the esophageal tissue drawn into the void of capsule 18 and disengages from capsule 18, thereby leaving capsule 18 attached to the wall of esophagus 14. Delivery device 22 may, for example, advance a locking pin through the esophageal tissue drawn into the void to anchor capsule 18 to the wall of esophagus 14.

While on the wall of esophagus 14, capsule 18 and, more particularly, the acidity sensor of capsule 18 obtains acidity measurements for a period of time, e.g., 24 hours, and relays the acidity measurements to receiver 20 via wireless telemetry. Capsule 18 eventually self-detaches from the wall of the esophagus and is passed through the digestive system of patient 12.

As will be described, prior to introducing delivery device 22 into patient 12, the pressure sensitive chamber is formed within or proximate to the distal end of probe 26. The pressure sensitive chamber can be formed within the inner lumen formed by probe 26 by closing vacuum inlet 34 and the vacuum outlet in accordance with the invention. As will be described in more detail, delivery device 22 can include a membrane that covers the vacuum outlet and a valve that is shut to close vacuum inlet 34. In this manner, the pressure sensitive chamber is formed within the distal portion of probe 26 and handle 24 of delivery device 22.

The distal end of probe 26 can be formed from a flexible material such that outside pressure applied to the distal end of probe 26 by the LES causes the flexible portion of probe 26 to deform, thereby varying the pressure within the pressure sensitive chamber. Alternatively, capsule delivery device 22 can include a balloon (not shown) that is filled with air to form the pressure sensitive chamber. As the pressure exerted on the outside of the balloon increases upon encountering the LED, the balloon deforms, thereby varying the pressure within the pressure sensitive chamber.

Although the techniques of the invention are described in terms of delivering a capsule 18 for sensing acidity of esophagus 14 of the patient, the techniques of the invention may be applied for delivery of other types of sensor to different tissue locations or organs.

Figure 2:
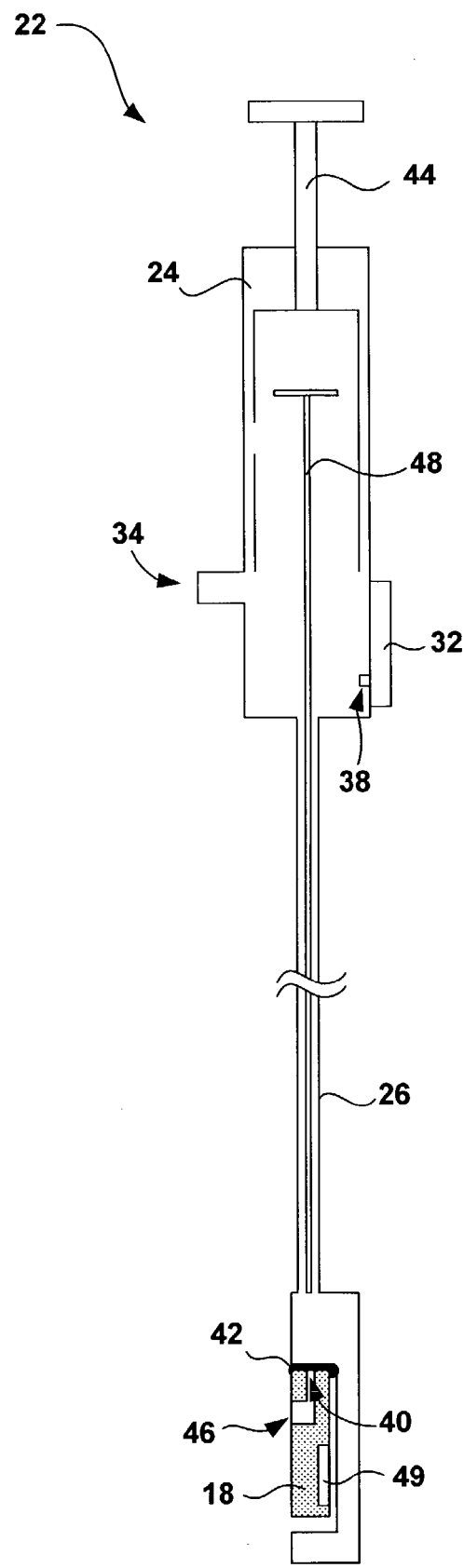
FIG. 2 is a schematic diagram illustrating an exemplary delivery device for anchoring a capsule to an esophagus of a patient for sensing the acidity of esophagus.

FIG. 2 is a schematic diagram illustrating an exemplary delivery device 22 for delivering a capsule 18 to an esophagus 14 of a patient for sensing the acidity of esophagus 14. In accordance with the invention, delivery device 22 is capable of measuring pressure variation within a pressure sensitive chamber in order to determine an appropriate location for placement of capsule 18. Delivery device 22 includes a handle 24 and a probe 26 that extends from handle 24. Capsule 18 is coupled to a distal end of probe 26 for delivery to a wall of esophagus 14. Delivery device 22 delivers capsule 18 to the appropriate location along esophagus 14 and anchors capsule 18 to the appropriate location.

Delivery device 22 includes a pressure sensor 38 to detect pressure variations within a pressure sensitive chamber of delivery device 22. Delivery device 22 further includes a display 32 located on handle 24 that displays the pressure measurements made by pressure sensor 38. As described above, display 32 may display pressure measurements with varying accuracy depending on the application. For example, to identify the location of the LES, display 32 may display relative pressure variations, e.g., using a number of LEDs that successively light up as the pressure increases. Pressure sensor 38 can comprise, for example, a piezoelectric pressure sensor, a capacitive pressure sensor, or any other sensor capable of detecting pressure variations. Handle 24 further incorporates appropriate electronics (not shown) to process the signals generated by pressure sensor 38 and drive display 32.

As described above, the pressure sensitive chamber may be formed within delivery device 22 by closing a vacuum inlet 34 and covering vacuum outlet 40 with a membrane 42. More specifically, delivery device 22 may include a controller 44 on handle 24 that controls opening and closing of vacuum inlet 34 and, thus, application of suction from vacuum 36. Controller 44 may further control the pressure monitoring capabilities of delivery device 22. In particular, controller 44 may power pressure sensor 38 and display 32 on and off. For example, controller 44 closes vacuum inlet 34 and activates pressure sensor 38 and display 32 before probe 26 of delivery device 22 is introduced into esophagus 14. Controller 44 may comprise a plunger that is successively pushed through different stages to perform sequential operations during the delivery of capsule 18 to the appropriate location along esophagus 14. Alternatively, controller 44 may comprise a dial, switch, or similar control mechanism that can be switched to different settings to perform different functions.

Membrane 42 covering vacuum outlet 40 may be constructed of a flexible material such as flexible plastic. Membrane 42 can be adhered over vacuum outlet 40 during manufacture of delivery device 22. Membrane 42 prevents air from escaping via vacuum outlet 40, in turn, making the pressure sensitive chamber airtight.

Membrane 42 within the distal end of probe 26 deforms due to pressure variations experienced within esophagus 14 and stomach 16, i.e., pressure variations caused by passage through the LES. For example, when the distal end of probe 26 is being retracted from stomach 16 into esophagus 14, membrane 42 deforms due to an increased pressure caused by retraction through the LES, in turn, causing a pressure variation within the pressure sensitive chamber. Pressure sensor 38 detects the pressure variation within the pressure sensitive chamber, i.e., the pressure variation caused by the deformation of the distal end of probe 26, and delivery device 22 conveys the pressure variation via display 32 to a user. In this manner, delivery device 22 identifies the location of the LES. Delivery device 22 can be further retracted to place the distal end of probe 26 at a desired location within the lower esophagus, e.g., 2 cm above the LES, for placement of capsule 18.

Upon identifying the appropriate location for placement of capsule 18, controller 44 opens vacuum inlet 34 and deactivates, i.e., shuts off, the pressure detection functionality of delivery device 22. Vacuum inlet 34 receives sufficient suction pressure from vacuum 36 to cause membrane 42 that covers vacuum outlet 40 to be removed. In other words, the suction pressure from the vacuum opens vacuum outlet 40 by removing or rupturing membrane 42. Membrane 42 covering vacuum outlet 40 may be completely removed by the suction pressure. For example, the suction pressure may have a larger force than the adhesive holding membrane 42 over vacuum outlet 40. Alternatively, the suction of the vacuum may, instead, rupture membrane 42 in order to open vacuum outlet 40.

Upon removal or rupture of membrane 42, the suction from the vacuum is further applied to vacuum outlet 40 to draw a portion of esophageal tissue into a void 46 of capsule 18. Upon drawing the esophageal tissue into void 46, controller 44 is adjusted to cause delivery device 22 to anchor capsule 18 to the esophageal tissue. More specifically, controller 44 can be adjusted to cause a shaft 48 to advance a locking pin (not shown) through the esophageal tissue within void 46 in order to anchor sensing capsule 18 to a wall of esophagus 14. For example, if controller 44 comprises a plunger, the plunger may be actuated into handle 24 in order to advance the locking pin through the esophageal tissue. However, any type of anchoring mechanism may be used to anchor capsule 18 to the esophageal tissue.

Capsule 18 detaches from delivery device 22 thereby leaving capsule 18 attached to the wall of esophagus 14.

Delivery device 22 is removed and an acidity sensor 49 of capsule 18 begins to measure acidity values of esophagus 14 over time and transmit the information to receiver 20 via wireless communication, i.e., via a transmitter and an antenna.

Figure 3:
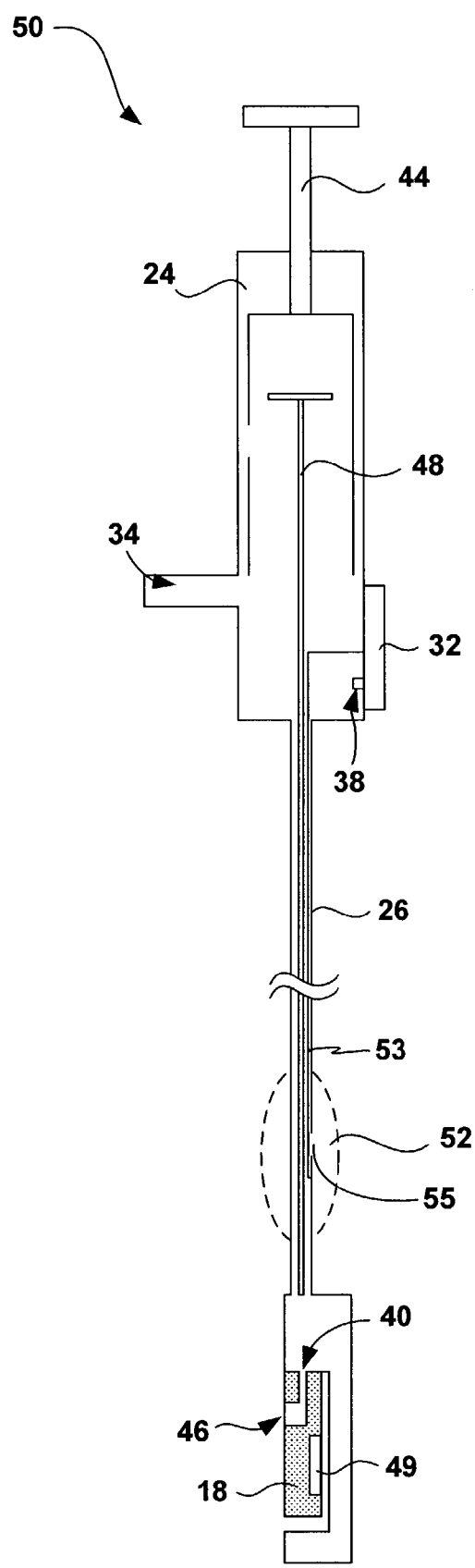
FIG. 3 is schematic diagram illustrating another exemplary delivery device for anchoring a capsule to an esophagus a patient for sensing acidity.

FIG. 3 is schematic diagram illustrating another exemplary delivery device 50 for anchoring a capsule 18 to an esophagus 14 a patient for sensing acidity. Delivery device 50 conforms substantially to delivery device 22 of FIG. 2, but delivery device 50 includes a balloon 52 that is at least partially filled to form the pressure sensitive chamber. Balloon 52 is in fluid communication with a separate lumen 53 than the lumen through which suction is applied via the vacuum. Because the balloon is in fluid communication with a separate lumen 53, via port 55, there is no longer a need for membrane 42 to cover vacuum outlet 40. Lumen 53, port 55, and balloon 52 are in fluid communication with pressure sensor 38.

Delivery device 50 detects the location of the LES in much the same manner as delivery device 22 of FIG. 2. Particularly, as balloon 52 passes from esophagus 14 into stomach 16 or vice versa, e.g., from stomach 16 to esophagus 14, balloon 52 deforms due to the pressure applied upon passing through the LES, in turn, causing a pressure variation within the pressure sensitive chamber. Pressure sensor 38 detects the pressure variation within the pressure sensitive chamber and displays the pressure change via display 32.

In some cases, balloon 52 may share a common lumen with vacuum 32, in which case a membrane 42 is needed to cover vacuum outlet 40. When sensing capsule 46 is in the correct position, determined by the appropriate pressure variations, suction is applied via the vacuum to remove or rupture membrane 42 as well as deflate balloon 52.

Figure 4:
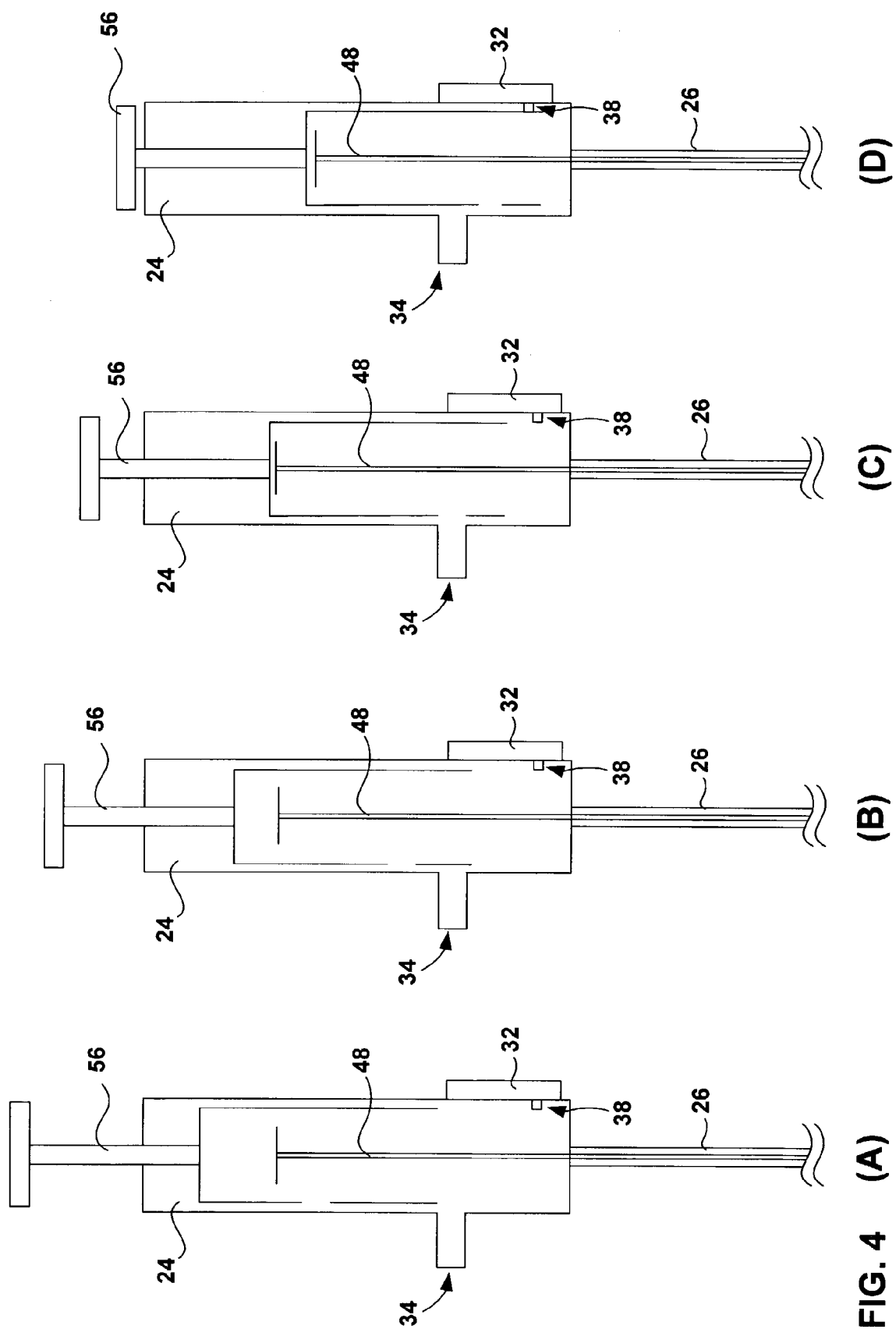
FIG. 4 is a block diagram illustrating a proximal end of delivery device anchoring a capsule to an esophagus of a patient.
Figure 5:
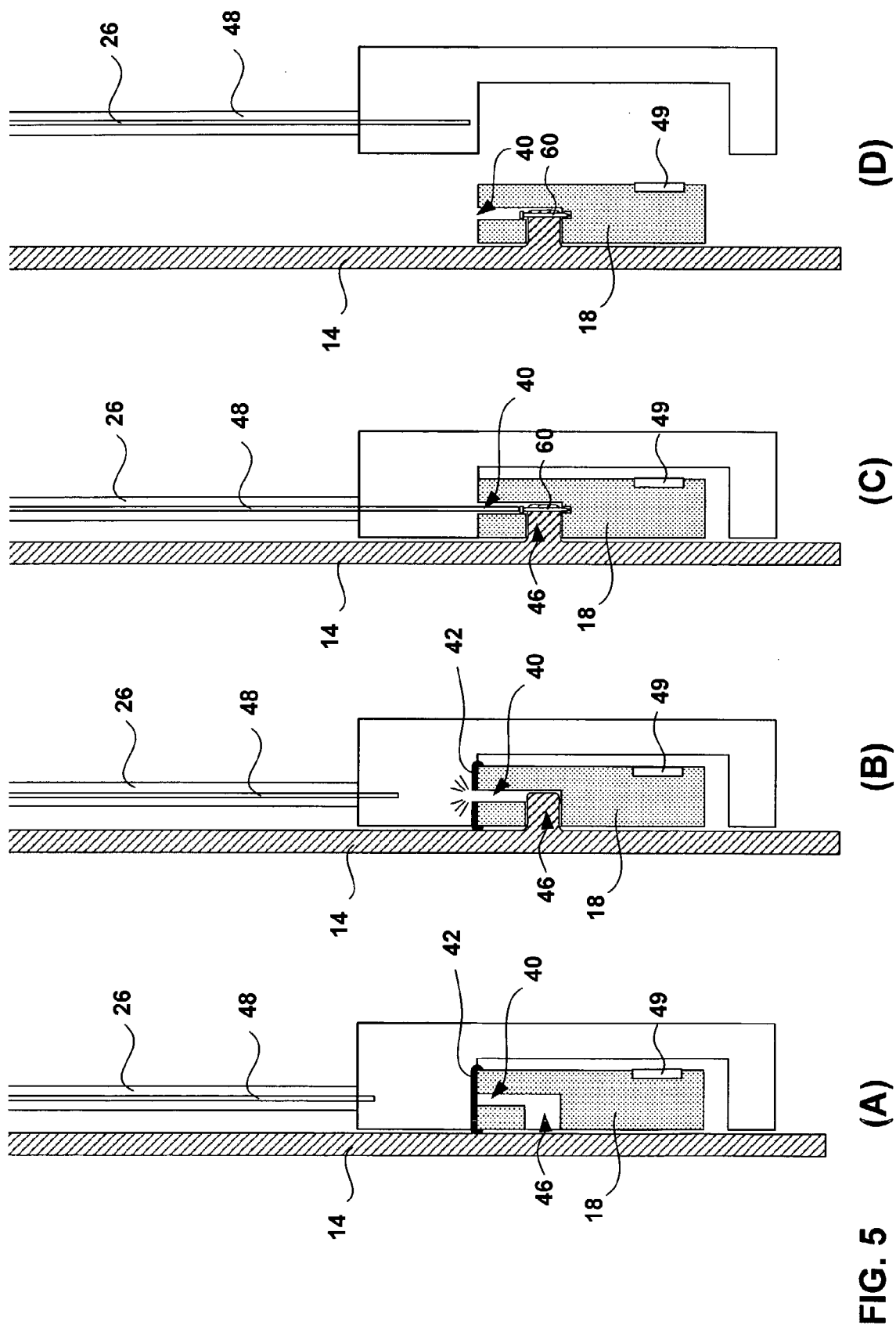
FIG. 5 is a block diagram illustrating a distal end of a delivery device anchoring a capsule to an esophagus of a patient.

FIG. 4 is a block diagram illustrating a proximal end of delivery device 22, i.e., handle 24, that includes a plunger 56 as a controller. Plunger 56 is pushed through different stages to in order to anchor capsule 18 (not shown) to esophagus 14. The corresponding actions that occur at a distal end of delivery device 22 in response to the stages illustrated in FIG. 4 are shown in FIG. 5.

Initially, plunger 56 of deliver device 22 is positioned such that the vacuum inlet is open (FIG. 4(A)). Vacuum inlet 34 is initially left open to prevent membrane 42 (FIG. 2) from rupturing during transportation to or from the hospital or clinic. Before introducing probe 26 of delivery device 22 into esophagus 14 of the patient, plunger 56 is advanced one stage to close vacuum inlet 34 and turn on the pressure sensing capabilities of delivery device 22 (FIG. 4(B)). In this manner, vacuum inlet 34 is closed to form a pressure sensitive chamber within delivery device 22. Further, display 32 and pressure sensor 38 are activated. Before introducing probe 26 of delivery device 22 into esophagus 14 of patient 12, the physician attaches a vacuum 36 to vacuum inlet 34. However, no suction is applied within the lumen formed by probe 26 because vacuum inlet 34 is closed. In the embodiment in which a balloon forms the pressure sensitive chamber, the balloon is partially filled with air at this stage.

The distal end of probe 26 enters esophagus 14, via either nasal cavity 28 or oral cavity 30, and extends through esophagus 14 into stomach 16 via the lower esophageal sphincter (LES). The distal end of probe 26 is slowly retracted back into esophagus 14 and the pressure variation due to the LES is detected to identify the appropriate location for capsule 18. Specifically, the pressure sensitive chamber experiences pressure variations, which are displayed to the physician via display 32, indicating the location of the LES.

Upon identifying the appropriate location for placement of capsule 18, plunger 56 is advanced to the next stage, which opens vacuum inlet 34 and deactivates, i.e., shut off pressure functionality of delivery device 22 (FIG. 4(C)). Vacuum inlet 34 receives suction pressure from vacuum 36 causing membrane 42 that covers vacuum outlet 40 to be either removed or ruptured to open vacuum outlet 40. As described above, the suction from the vacuum draws esophageal tissue of the wall of esophagus 14 into void 46 of capsule 18.

Plunger 56 is advanced another stage further, in turn contacting and advancing shaft 48 to drive a locking pin or other anchor mechanism through the esophageal tissue in void 46 of capsule 18 in order to anchor capsule 18 to esophagus 14 (FIG. 4(D)). Delivery device 22 may then be removed from esophagus 14 of patient 12.

FIG. 5 is a block diagram illustrating a distal end of a delivery device 22 anchoring a capsule 18 to esophagus 14. Particularly, FIGS. 5(A)-(D) corresponding to actions that occur at the proximal end of delivery device 22 as illustrated in FIGS. 4(A)-(D). Specifically, FIG. 5(A) illustrates the distal end of delivery device 22 with membrane 42 covering vacuum outlet 40 to provide a pressure sensitive chamber for identifying an appropriate location for attachment of capsule 18. FIG. 5(B) illustrates application of suction via opening of a vacuum inlet 34 (FIG. 4B) to remove or rupture membrane 42. FIG. 5(B) also illustrates the suction from a vacuum coupled to delivery device 22 drawing in a portion of esophageal tissue from the wall of esophagus 14 into void 46 of capsule 18. FIG. 5(C) illustrates anchoring of capsule 18 to the wall of esophagus 14 via advancement of a locking pin 60 through the esophageal tissue drawn into void 46 of capsule 18. FIG. 5(D) illustrates the detachment of capsule 18 from delivery device 22 and the removal of delivery device 22 from esophagus 14.

Figure 6:
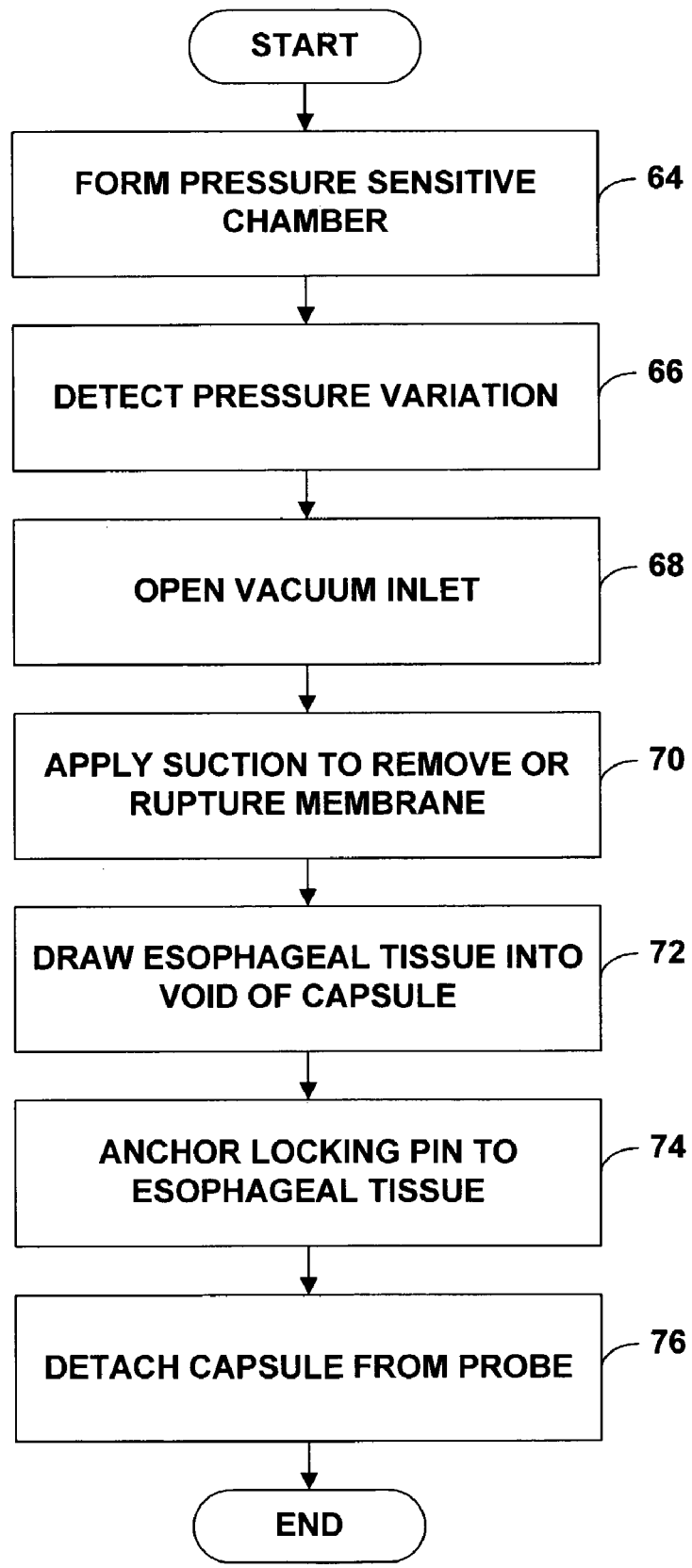
FIG. 6 is a flow diagram illustrating operation of delivery device delivering a capsule to an appropriate location along esophagus in accordance with the invention.

FIG. 6 is a flow diagram illustrating operation of delivery device 22 delivering capsule 18 to an appropriate location along esophagus 14 in accordance with the invention. Initially, delivery device 22 forms a pressure sensitive chamber to detect pressure variations indicating an appropriate location for placement of a capsule 18 (64). In one embodiment, delivery device 22 includes a membrane 42 that covers a vacuum outlet and the pressure sensitive chamber is formed by closing vacuum inlet of delivery device 22 to form an airtight chamber. In another embodiment, the pressure sensitive chamber is formed by filling a balloon 52 with air.

Delivery device 22 detects pressure variations within the pressure sensitive chamber in order to determine the location of the LES and, in turn, the appropriate location for anchoring of capsule 18 (66). Particularly, the distal end of probe 26 enters esophagus 14, via either nasal cavity 28 or oral cavity 30, and extends through esophagus 14 into stomach 16 via the LES. The distal end of probe 26 is slowly retracted back into esophagus 14 and the pressure variation due to the LES is detected to identify the appropriate location for capsule 18. Specifically, the pressure applied by the LES deforms the distal end of probe 26 or balloon 52, thereby causing a pressure variation within the pressure sensitive chamber. In addition, delivery device 22 conveys the pressure variation to the physician via a display 32.

Upon identifying the appropriate location for anchoring of capsule 18, delivery device 22 opens vacuum inlet 34, which receives suction pressure from vacuum 36 (68). The suction applied via the vacuum causes membrane 42 covering vacuum outlet 40 to rupture or be completely removed, in turn, opening vacuum outlet 40 (70). The suction applied by the vacuum further draws esophageal tissue into a void of capsule 18 (72).

Delivery device 22 anchors capsule 18 to the wall of esophagus 14 using an anchoring mechanism, such as a locking pin (74). For example, delivering device 22 may advance the locking pin through the esophageal tissue in the void of capsule 18 to anchor capsule 18 to the wall of esophagus 14. Upon anchoring capsule 18 to esophagus 14, capsule 18 is detached from delivery device 22, thereby leaving capsule 18 leaving capsule 18 anchored to esophagus 14 (76). While anchored on the wall of esophagus 14, capsule 18 and, more particularly, the acidity sensor of capsule 18 obtains acidity measurements within esophagus 14 and relays the acidity measurements to receiver 20 via wireless telemetry.

Various embodiments of the invention have been described. These and other embodiments are within the scope of the following claims.

What is claimed is:

1. A device for identifying a location within a patient for delivery of a capsule, the device comprising:
    a probe that defines an inner lumen;
    a capsule detachably coupled to a distal end of the probe that includes a sensor;
    a pressure sensitive chamber within the inner lumen of the probe;
    a vacuum inlet at a proximal end of the probe that couples with a vacuum source;
    a vacuum outlet located at the distal end of the probe;
    a membrane that covers the vacuum outlet; and
    a pressure sensor to detect pressure variation within the pressure sensitive chamber indicative of proximity to a sphincter within the patient to identify a location for delivery of the capsule, wherein the vacuum inlet, when closed, forms the pressure sensitive chamber within the inner lumen of the probe, and the vacuum inlet, when opened, permits application of suction from the vacuum source within the inner lumen of the probe in order to remove or rupture the membrane that covers the vacuum outlet.

2. The device of claim 1, wherein the membrane is formed from a flexible material and deforms due to outside pressure changes to cause a pressure variation within the pressure sensitive chamber.

3. The device of claim 1, further comprising a balloon that expands to form the pressure sensitive chamber.

4. The device of claim 1, further comprising a display at a proximal end of the device to display the pressure variations detected by the pressure sensor.

5. The device of claim 4, wherein the display comprises one of a liquid crystal display (LCD) and a light emitting diodes (LED) display.

6. The device of claim 1, wherein the capsule defines a void and the vacuum source provides suction to the vacuum outlet to draw a portion of esophageal tissue into the void of the capsule, further comprising an anchor mechanism to penetrate the portion of esophageal tissue in the void of the capsule in order to anchor the capsule to the esophageal tissue.

7. The device of claim 6, wherein the anchor mechanism comprises a locking pin that advances through the esophageal tissue to anchor the capsule to the esophageal tissue.

8. The device of claim 1, further comprising a switch to switch the pressure sensor on.

9. The device of claim 1, further comprising a valve that opens and closes the vacuum inlet of the device.

10. The device of claim 1, wherein the sensor comprises an acidity sensor to detect the acidity of a surrounding location.

11. A method for delivering a capsule within a patient, the method comprising:
    inserting at least a portion of a probe into the patient;
    forming a pressure sensitive chamber within the probe for detecting pressure variations within the patient, wherein the probe has a vacuum outlet and a vacuum inlet, the vacuum outlet being covered by a membrane, and wherein forming the pressure sensitive chamber comprises closing the vacuum inlet;
    detecting pressure variation within the pressure sensitive chamber of the probe, said pressure variation being indicative of proximity to a sphincter of the patient, opening the vacuum inlet to provide suction within the probe;
    removing or rupturing the membrane that covers the vacuum outlet via the suction;
    providing the suction to a tissue site of the patient to draw a portion of the tissue site into a void of a capsule coupled to a distal end of the probe in response to detecting the pressure variation indicative of proximity to the sphincter;
    anchoring the capsule to the tissue site; and
    detaching the capsule from the probe.

12. The method of claim 11, wherein the capsule includes a sensor and further comprising:
    measuring at least one parameter of the tissue site via the sensor of the capsule; and
    transmitting the measured parameters from the capsule to a receiver.

13. The method of claim 12, wherein the sensor comprises an acidity sensor and the parameter comprises pH information.

14. The method of claim 11, wherein the membrane is formed from a flexible material and deforms due to outside pressure changes to cause the detected pressure variation.

15. The method of claim 11, wherein forming a pressure sensitive chamber comprises filling a balloon with air to form the pressure sensitive chamber.

16. The method of claim 15, wherein the balloon deforms due to outside pressure changes to cause the detected pressure variation.

17. The method of claim 11, further comprising displaying the pressure variation to a user.

18. The method of claim 11, wherein detecting a pressure variation within a pressure sensitive chamber comprises detecting a pressure variation due to transitioning from a stomach to an esophagus via a lower esophageal sphincter (LES).

19. The method of claim 11, wherein anchoring the capsule to the tissue site comprises advancing a locking pin through the portion of the tissue site in the void of the capsule.

20. The method of claim 11, wherein the tissue site comprises the esophagus.

* * * * *